United States Patent
Sato et al.

(10) Patent No.: US 6,316,660 B1
(45) Date of Patent: *Nov. 13, 2001

(54) PROCESS FOR PRODUCING CYCLOHEXYLAMINO ACIDS

(75) Inventors: Takahiro Sato; Yutaka Honda; Kunisuke Izawa, all of Kawasaki (JP)

(73) Assignee: Ajinomoto Co., Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/908,430

(22) Filed: Aug. 7, 1997

(30) Foreign Application Priority Data

Aug. 7, 1996 (JP) .................................................. 8-208029

(51) Int. Cl.[7] ........................... C07C 209/00; C07C 61/08
(52) U.S. Cl. ............................................ 560/125; 562/507
(58) Field of Search ............................... 560/43, 44, 125; 562/433, 507

(56) References Cited

U.S. PATENT DOCUMENTS

| 4,048,222 | * | 9/1977 | Saito et al. | 260/514 J |
| 5,107,053 | * | 4/1992 | Wu | 560/19 |
| 5,334,758 | * | 8/1994 | Saburi et al. | 562/590 |

FOREIGN PATENT DOCUMENTS 1 290 923   9/1972 (GB) ........................... C07C/108/18

OTHER PUBLICATIONS

Derwent Abstracts, AN 77–41256Y, SU 526 616, Dec. 7, 1976.
Paul Francis Schuda, et al., Journal of Organic Chemistry, American Chemical Society, vol. 53, No. 4, pp. 873–875, "A Short and Efficient Synthesis Of (3S, 4S)–4–[(Tert–Butyloxycarbonyl)Amino]–5–Cyclohexyl–3–Hydroxypentanoic Acid Ethyl Ester", Feb. 19, 1988.
M. Tamura, et al., Synthetic Communications, vol. 8, No. 5, pp. 345–351, "A Synthesis Of Optically Active α–cyclohexylglycine", 1978.

* cited by examiner

*Primary Examiner*—Rosalynd Keys
(74) *Attorney, Agent, or Firm*—Oblon, Spivak, McClelland, Maier & Neustadt, P.C.

(57) ABSTRACT

A process for producing optically active amino acid derivatives having a cyclohexyl group or a substituted cyclohexyl group by hydrogenating an amino acid derivative containing an aromatic group in the presence of a ruthenium catalyst. The starting material may be an unprotected amino acid or an N- and/or C-protected derivative thereof. An major advantage of the process is that the reduction may be accomplished without substantial racemization.

35 Claims, No Drawings

PROCESS FOR PRODUCING CYCLOHEXYLAMINO ACIDS

BACKGROUND OF THE INVENTION

1. Field of the Invention

The present invention relates to a process for producing optically active amino acid derivatives having a cyclohexyl group. The products of the present process are important intermediates in the preparation of pharmaceuticals, such as renin inhibitors.

2. Discussion of the Background Art

A cyclohexyl group-containing amino acid is a residue of a renin inhibitor as described in WO 91/07430, EP 438311, EP 427939 and Japanese Laid-Open (Kokai) No. 9,162/1993. Since this compound is a synthetic derivative, it has aroused much interest with respect to its pharmacological activity.

A method of synthesizing a cyclohexyl group-containing amino acid is known per se. This known method produces a racemic compound. Although this method uses an optically active starting material, the optical purity of the resulting amino acid is unclear. Therefore, this method fails to produce an optically active amino acid product. This method also suffers from a low reaction yield and uses a solvent that is difficult to manipulate on an industrial scale.

Specific examples of the production of an amino acid which is optically active and contains a cyclohexyl group include the production of cyclohexylalanine by reducing L-phenylalanine in an aqueous acetic acid solution using a platinum oxide catalyst (J. Org. Chem., 1988, 53, 873 and Tetrahedron, 1992, 48, 307), and the production of cyclohexylglycine by reducing (R)-phenylglycine in a carbon-containing aqueous solution using a palladium hydroxide catalyst (Synth. Commun., 1978, 8, 345). However, in the former case, the optical purity of the product is unclear. In the latter case, the yield is as low as between 24 and 66%, and cyclohexyl acetate is formed as a by-product at a ratio of from 27 to 68%. Further, the optical purity of the resulting cyclohexylglycine is between 66 and 84% ee, which is not satisfactory. Accordingly, these methods are not useful on an industrial scale.

Incidentally, in the reduction of an aromatic hydrocarbon compound, the reaction is generally conducted at a hydrogen pressure in the presence of a catalyst such as rhodium, ruthenium, platinum or the like using an alcohol or the like as a solvent. With an unsubstituted aromatic hydrocarbon compound, the reaction proceeds relatively easily using a rhodium catalyst. However, with a hydrocarbon compound having a substituted aromatic ring, the reaction hardly proceeds owing to the influence of the resonance of the ring, or a side effect such as hydrogenolysis of a substituent or the like occurs. Thus, detailed studies on the reaction conditions are required in many cases (see, for example, J. Org. Chem., 1958, 23, 276 and Org. Syn., 1947, 27, 21).

With respect to reduction of an aromatic ring of an aromatic compound having a substituent with an asymmetric carbon atom, it is reported that optically active mandelic acid is reduced in the presence of a rhodium catalyst (J. Org. Chem., 1962, 27, 2288). This document describes that the racemization is suppressed almost completely. However, product crystals having an optical purity of 92% ee are obtained from a starting material having an optical purity of 95% ee. Thus, a loss of optical purity of several percent by racemization appears unavoidable with this process. Regarding the racemization of mandelic acid, it is considered that the substituent in the benzyl position participates in the reaction as in the reduction (R)-phenylglycine, described above, to form a conjugated system relative to the benzyl position, with the result that the side reaction occurs with racemization. Consequently, reducing the aromatic ring of optically active phenylglycine while maintaining the optical purity thereof is especially difficult.

It has been reported that a ketone group in L-cyclohexylalanine derivatives is reduced in an alcohol solvent in the presence of a Raney nickel catalyst (J. Org. Chem., 1988, 53, 873). However, in spite of mild conditions, racemization occurred at a ratio of 15% simultaneously with the reduction of the ketone moiety. It appears extremely difficult to avoid racemization during hydrogenation of amino acids containing aromatic rings.

SUMMARY OF THE INVENTION

An object of the present invention is to provide an industrial process for producing optically active amino acid derivatives having a cyclohexyl group by reduction of the corresponding aromatic group containing amino acids, preferably in high yield and without substantial racemization.

The present inventors have conducted investigations to solve the above-mentioned problems, and have consequently invented a process for producing amino acids having a cyclohexyl group in high yields without substantial racemization by catalytically reducing aromatic amino acids using a ruthenium catalyst.

The present invention provides a process for producing an amino acid derivative represented by formula (I):

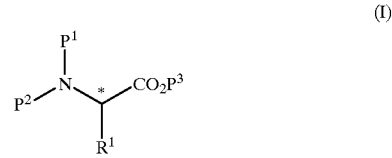

where $R^1$ is an unsubstituted or substituted cyclohexyl group having from 6 to 15 carbon atoms or an unsubstituted or substituted cyclohexylalkyl group having from 7 to 15 carbon atoms;

$P^1$ and $P^2$ are each, independently, a hydrogen atom or an amino-protecting group, or $P^1$ and $P^2$ together form a difunctional amino-protecting group;

$P^3$ is a hydrogen atom or a carboxyl-protecting group; and

* is an asymmetric carbon atom, by hydrogenating an aromatic amino acid represented by formula (II) in the presence of a ruthenium catalyst:

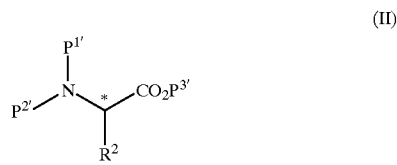

where $R^2$ is an unsubstituted or substituted aryl group having from 6 to 15 carbon atoms or an unsubstituted or substituted aralkyl group having from 7 to 15 carbon atoms;

$P^{1'}$ and $P^{2'}$ are each, independently, a hydrogen atom or an amino-protecting group, or $P^{1'}$ and $P^{2'}$, together, form a difunctional amino-protecting group;

$P^{3'}$ is a hydrogen atom or a carboxyl-protecting group; and

* is as defined above.

DETAILED DESCRIPTION OF THE INVENTION

The aromatic amino acid derivative represented by formula (II) used as the starting material in the present invention may be a natural or a synthetic compound. Compound (II) may be an unprotected amino acid or an N- and/or C-protected derivative thereof. N- and C-protecting groups for amino acids are well-known. A detailed description of suitable protecting groups is provided by T. W. Greene and P. G. M. Wuts, Protective Groups in Organic Synthesis, Second Edition, John Wiley and Sons, 1991. Pages 224–276 and 309–405 of this document are incorporated herein by reference. Examples of protected aromatic amino acid derivatives include those where the amino group is protected with, for an example, a carbamate, amide, or hydrocarbon group, derivatives where the carboxyl group is protected as, for example, an ester, and N-protected amino acid esters obtained by protecting both the amino group and the carboxyl group. Preferably, the N- and C-protecting groups have 1 to 25 carbon atoms, inclusive of all specific values and subranges therebetween.

In formula (II), $P^{1'}$ and $P^{2'}$ are, independently, a hydrogen atom or a monofunctional amino protecting group. Alternatively, $P^{1'}$ and $P^{2'}$ may together form a difunctional amino-protecting group. These protecting groups may be stable to the reaction conditions used to reduce the aromatic ring, i.e., $P^1$ and/or $P^2$ in formula (I) are the same as $P^{1'}$ and/or $P^{2'}$. Alternatively, the protecting groups may be removed during the reduction and thereby be converted to a hydrogen atom, i.e., $P^1$ and/or $P^2$ are hydrogen atoms. Of course, when $P^{1'}$ and/or $P^{2'}$ is a hydrogen atom, then $P^1$ and/or $P^2$ in formula (I) is a hydrogen atom as well. Examples of amino-protecting groups which are stable to the reduction include the tert-butoxycarbonyl group, acetyl group, formyl group, trifluoroacetyl group and phthaloyl groups. Amino-protecting groups which may be cleaved during the reduction include the benzyloxycarbonyl group and benzyl groups (a dibenzyl-protected amine, i.e, $P^{1'}$ and $P^{2'}$ are each a benzyl group, is particularly preferred).

$P^{3'}$ may be a hydrogen atom. Alternatively, $P^{3'}$ may be a carboxyl protecting group, i.e., —$CO_2P^{3'}$ defines a protected carboxylic acid group. When $P^{3'}$ is a carboxyl protecting group, it may be stable to the reaction conditions used to reduce the aromatic ring, i.e., $P^3$ in formula (I) is the same as $P^{3'}$. Alternatively, the protecting group may be cleaved during the reduction and thereby be converted to a hydrogen atom, i.e., $P_3$ in formula (I) is a hydrogen atom. Suitable carboxyl protecting groups which are stable to the reduction of the aromatic ring include an ethyl ester group, a methyl ester group and a tert-butyl ester group. An example of a carboxyl protecting group that may be removed in the reduction includes is the benzyl ester group. Of course, when $P^{3'}$ is a hydrogen atom, $P^3$ in formula (I) is also a hydrogen atom.

In the present method, the $R^2$ group in formula (II) is reduced to produce the $R^1$ group in formula (I). $R^2$ may be an unsubstituted or substituted aryl group having 6 to 15 carbon atoms. Alternatively, $R^2$ is an unsubstituted or substituted aralkyl group having 7 to 15 carbon atoms. Preferably, $R^2$ contains a phenyl group. A preferred aralkyl group is a phenylalkyl group. The aryl group may be substituted. Suitable substituents include alkyl groups (such as $C_{1-10}$ groups, which may have any structure, i.e., linear, branched or cyclic), alkoxy groups (where the alkyl moiety may have 1 to 10 carbon atoms and may have any structure, i.e., linear, branched or cyclic), alkoxyalkyl groups (preferably having 2 to 10 carbon atoms), hydroxyl groups, amino groups, nitro groups (which may be reduced to amino groups during the reduction), carboxylic acids and carboxylic esters (such as those having 2–10 carbon atoms). The aryl group may have multiple substituents. Preferably, the aryl group has one, two or three substituents.

Examples of unprotected aromatic amino acids that may be used in the present process include L-phenylalanine, D-phenylalanine, D-phenylglycine, L-phenylglycine, L-tyrosine and D-tyrosine. These amino acids may be N- and/or C-protected as described above.

As used herein, the term "optical purity" refers to the enantiomeric excess of one optical isomer over the other in terms of % ee. The optical purity of starting material (II) is preferably greater than 0% ee and may be up to and including 100% ee. Preferably, the optical purity of (II) is at least 50% ee, more preferably at least 75% ee, even more preferably at least 85% ee, still even more preferably at least 95% ee, and, most preferably, at least 99% ee. These ranges in optical purity include all specific values and subranges therebetween, including 1, 5, 10, 20, 30, 40, 60, 99.1, 99.2, 99.3, 99.4, 99.5, 99.6, 99.7, 99.8, 99.9, 99.95, 99.98 and 99.99% ee.

The optical purity of the product (I) is preferably greater than 0% and may be up to and including 100% ee. Preferably, the optical purity of (I) is at least 0% ee, more preferably at least 75% ee, even more preferably at least 85% ee, still even more preferably at least 95% ee, and, most preferably, at least 99% ee. These ranges in optical purity include all specific values and subranges therebetween, including 1, 5, 10, 20, 30, 40, 60, 99.1, 99.2, 99.3, 99.4, 99.5, 99.6, 99.7, 99.8, 99.9, 99.95, 99.98 and 99.99% ee.

An important advantage of the present process is that the loss of optical purity in the reduction may be very small. In fact, there may be no detectable loss of optical purity. The percent reduction in optical purity during the reaction is defined as the difference between the optical purity (% ee) of (II) and the optical purity (% ee) of (I). For example, if (II) is enantiomerically pure, i.e., 100% ee, and the product (I) has an optical purity of 90% ee, then the percent reduction in optical purity is 100%–90%=10%. Preferably, the percent reduction in optical purity is at most 10%, more preferably at most 5%, even more preferably at most 2%, still even more preferably at most 1% and, most preferably, at most 0.5%. These ranges include all specific values and subranges therebetween, including 0.9, 0.8, 0.7, 0.6, 0.5, 0.4, 0.3, 0.2, 0.1, 0.05, and 0.02% reduction of optical purity in the reduction of (II) to (I).

The protected aromatic amino acid derivatives may easily be synthesized by any well-known method. Detailed synthetic procedures are provided by T. W. Greene and P. G. M. Wuts, Protective Groups in Organic Synthesis, Second Edition, John Wiley and Sons, 1991.

The reduction is preferably conducted in solution. The solvent may comprise water or an alcohol. When the starting material (II) is an unprotected amino acid, i.e., $P^{1'}$, $P^{2'}$ and $P^{3'}$ are each hydrogen, the reaction is preferably conducted through stirring in an aqueous solution containing at least 1 equivalent of a base in the presence of hydrogen and the ruthenium catalyst. When the starting material is an N-protected amino acid, the reaction easily proceeds through stirring in an aqueous solution or an alcohol solution in the presence of hydrogen and the ruthenium catalyst. Suitable alcohols that may be used as the solvent include methanol, ethanol, isopropanol, n-butanol, sec-butanol, tert-butanol and octanol. The reaction in an alcohol may be conducted in the presence of base, preferably with at least 1 equivalent of the base. It is particularly preferred to used a base when the reaction is conducted in an aqueous solution. Preferably, at least one equivalent of base is used. Unless otherwise specified, the equivalents of base are relative to the equivalents of starting material (II) used in the hydrogenation.

Examples of the base used in the reduction include alkali metal hydroxides (such as sodium and potassium hydroxide) and ammonia. The amount of the base is preferably between 1 and 10 equivalents, more preferably between 1 and 2 equivalents. The concentration of the base in the solvent is, for example, between 0.1 and 2.0 N. The number of equivalents of base and the concentration of the base in the solvent include all specific values and subranges therebetween.

Any of the well-known ruthenium catalysts for hydrogenation may be used in the present invention. Suitable ruthenium catalysts include 1 to 10% ruthenium on carbon. The ruthenium catalyst is preferably used in an amount of from 0.001 to 0.1 equivalents, based on the amount of the starting amino acid derivative of formula (II). The hydrogen pressure during the reduction is preferably from 1 to 100 atm, inclusive of all specific values and subranges therebetween.

The reaction temperature is between room temperature and 250° C., preferably between 40 and 150° C. The reaction may be completed in 1 to 24 hours. These temperature and time ranges include all specific values and subranges therebetween.

After the reduction, the reaction solution may be filtered to remove the catalyst. Subsequently, when the reaction is conducted in a basic aqueous solution, the residue may be neutralized or acidified to precipitate the product in the form of a free substance or a salt. Suitable acids for neutralization or acidification include mineral acids (such as hydrochloric, sulfuric, nitric and phosphoric acid) and organic acids (such as formic, acetic and citric acid). Thus, the final product can easily be isolated and purified. The isolated product may be then be incorporated into peptides and proteins using well-established synthetic methodology.

EXAMPLES

Having generally described this invention, a further understanding can be obtained by reference to certain specific examples which are provided herein for purposes of illustration only and are not intended to be limiting unless otherwise specified.

The temperature is indicated in terms of a centigrade temperature unless otherwise instructed. Proton nucleic magnetic resonance spectrum were recorded on a Varian 300 MHz spectrometer with the chemical shifts (δ) listed as ppm. The analysis of N-unprotected amino acid optical isomers was conducted using a Shimadzu Optical Analysis Gas Chromatography DLAA-1 (column: Chirasil Val/ASA) System. The isomers were determined from areas (%) on a chart given by automatic derivatization into N-trifluoroacetyl and isopropyl esters and analysis thereof.

Example 1

L-cyclohexylalanine-hydrochloride

L-phenylalanine (2.010 g, 12.2 mmols) and 105.1 mg (0.05 mmols) of 5% ruthenium on active carbon as a catalyst were dissolved in 15 ml of a 1 N sodium hydroxide aqueous solution, and the solution was stirred at 60° C. and a hydrogen pressure of 30 kg/ $cm^2$ for 4.5 hours. The analysis of the reaction solution by HPLC revealed that the reduction proceeded quantitatively. With respect to the optical purity at this point, the area ratio was found to be L:D=99.5:0.5 as a result of the analysis through optical analysis gas chromatography. After the completion of the reaction, the reaction mixture was filtered through Celite to remove the ruthenium on active carbon. Thus, a sodium hydroxide solution of cyclohexylalanine was obtained. The resulting filtrate was concentrated to approximately ⅓ of the original volume under reduced pressure. Then, 11 ml (66 mmols) of a 6 N hydrochloric acid aqueous solution and 12.8 ml of water were added to the residue. The mixture was dissolved while being heat-stirred, and then precipitated through cooling to give 1.681 g (98.3% by weight, 7.96 mmols) of L-cyclohexylalanine hydrochloride in a yield of 65.2%.

As a result of the analysis through optical analysis gas chromatography, the area ratio was found to be L:D=99.7:0.3 (99.7% ee).

1H-NMR ($D_2O$)δ:0.88–1.08 (m, 2H), 1.15–1.34 (m, 3H), 1.34–1.52 (m, 1H), 1,58–1.86 (m, 7H), 3.89 (dd, 1H).

Example 2

(S)-cyclohexylglycine-hydrochloride (S)-phenylglycine (1.966 g, 13.0 mmols) and 106.6 mg (0.05 mmols) of 5% ruthenium on active carbon as a catalyst were dissolved in 15 ml of a 1 N sodium hydroxide aqueous solution. The solution was then stirred at 60° C. and a hydrogen pressure of 30 kg/$cm^2$ for 5 hours. The analysis of the reaction solution through HPLC revealed that the reduction proceeded quantitatively. At this time, as a result of the analysis through optical analysis gas chromatography, the area ratio was found to be S:R=99.2:0.8. After the completion of the reaction, the reaction mixture was filtered through Celite to remove the ruthenium on active carbon as a catalyst and obtain a sodium hydroxide solution of cyclohexylglycine. The resulting filtrate was concentrated to approximately ⅓ of the original volume under reduced pressure, and 11.2 ml (67.2 mmols) of a 6 N hydrochloric acid aqueous solution and 1 ml of water were added to the residue. The mixture was dissolved while being heat-stirred, and was precipitated through cooling to give 1.678 g (100% by weight, 8.7 mmols) of (S)-cyclohexylglycine hydrochloride in a yield of 65.4%. As a result of analysis through optical analysis gas chromatography, the area ratio was found to be S=>99.98 (R=<0.02) (>99.98% ee)

1H-NMR ($D_2O$)δ:1.05–1.37 (m, 5H), 1.62–1.81 (m, 5H), 1.93–2.03 (m, 1H), 3.82 (d, 1H).

Obviously, additional modifications and variations of the present invention are possible in light of the above teachings. It is therefore to be understood that within the scope of the appended claims, the invention may be practiced otherwise than as specifically described herein.

This application is based on Japanese Application No. 208029/1996, filed on Aug. 7, 1996, and incorporated herein by reference in its entirety.

What is claimed as new and is desired to be secured by Letters Patent of the United States is:

1. A process for producing an amino acid derivative represented by formula (I):

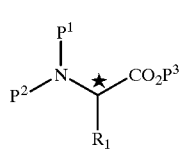

wherein:
$R^1$ represents an unsubstituted or substituted cyclohexyl group having 6 to 15 carbon atoms or an unsubstituted or substituted cyclohexylalkyl group having 7 to 15 carbon atoms;
$P^1$ and $P^2$ each, independently, represent a hydrogen atom or an amino-protecting group, or $P^1$ and $P^2$ together form a difunctional amino-protecting group;
$P^3$ represents a hydrogen atom or carboxyl-protecting group; and
★ represents an asymmetric carbon atom, comprising:
hydrogenating an aromatic amino acid derivative represented by formula (II) in the presence of a ruthenium catalyst in a solvent containing a base:

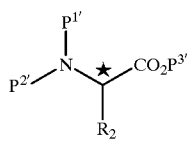

wherein:
$R^2$ represents an unsubstituted or substituted aryl group having 6 to 15 carbon atoms or an unsubstituted or substituted aralkyl group having 7 to 15 carbon atoms;
$P^{1'}$ and $P^{2'}$ each, independently, represent a hydrogen atom or an amino-protecting group, or a $P^{1'}$ and $P^{2'}$, together, form a difunctional amino-protecting group;
$P^{3'}$ represents a hydrogen atom or a carboxyl-protecting group; and
★ is as defined above.

2. The process of claim 1, wherein the solvent comprises water or an alcohol.

3. The process of claim 2, wherein the solvent comprises water.

4. The process of claim 3, wherein $P^1$, $P^2$, $P^3$, $P^{1'}$, $P^{2'}$ and $P^{3'}$ are each a hydrogen atom.

5. The process of claim 3, wherein the solvent contains at least one equivalent of the base.

6. The process of claim 3, wherein $P^3$ and $P^{3'}$ are each a hydrogen atom.

7. The process of claim 2, wherein the solvent comprises the alcohol.

8. The process of claim 7, wherein at least one of $P^{1'}$ and $P^{2'}$ represents an amino-protecting group, or $P^{1'}$ and $P^{2'}$, together, form a difunctional amino-protecting group.

9. The process of claim 7, wherein the solvent contains at least one equivalent of the base.

10. The process of claim 1, wherein either at least one of $P^{1'}$ or $P^{2'}$ represents an amino-protecting group, or $P^{1'}$ and $P^{2'}$, together, form a difunctional amino-protecting group.

11. The process of claim 1, wherein $P^{1'}$ and $P^{2'}$ are each a hydrogen atom.

12. The process of claim 1, wherein $P^3$ and $P^{3'}$ are each a hydrogen atom.

13. The process of claim 1, wherein $P^1$, $P^2$, $P^3$, $P^{1'}$, $P^{2'}$ and $P^{3'}$ are each a hydrogen atom.

14. The process of claim 1, wherein the asymmetric carbon atom in formula (I) and (II) has an S-configuration.

15. The process of claim 1, wherein the asymmetric carbon atom in formula (I) and (II) has an R-configuration.

16. A process for producing an amino acid derivative represented by formula (I):

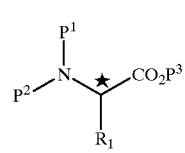

wherein:
$R^1$ represents an unsubstituted or substituted cyclohexyl group having 6 to 15 carbon atoms or an unsubstituted or substituted cyclohexylalkyl group having 7 to 15 carbon atoms;
$P^1$ and $P^2$ each, independently, represent a hydrogen atom or an amino-protecting group, or $P^1$ and $P^2$ together form a difunctional amino-protecting group;
$P^3$ represents a hydrogen atom or carboxyl-protecting group; and
★ represents an asymmetric carbon atom, comprising:
hydrogenating all aromatic amino acid derivative of formula (II) below ranging in enantiomer constituency from a racemic mixture to 100% single enantiomer in the presence of a ruthenium catalyst in a solvent containing a base such that as a result of reduction, the loss of optical purity of the amino acid product (I) does not exceed 10%:

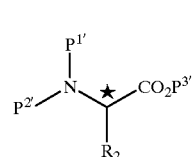

wherein:
$R^2$ represents an unsubstituted or substituted aryl group having 6 to 15 carbon atoms or an unsubstituted or substituted aralkyl group having 7 to 15 carbon atoms;
$P^{1'}$ and $P^{2'}$ each, independently, represent a hydrogen atom or an amino-protecting group, or a $P^{1'}$ and $P^{2'}$, together, form a difunctional amino-protecting group;
$P^{3'}$ represents a hydrogen atom or a carboxyl-protecting group; and
★ is as defined above.

17. The process of claim 16, wherein the loss of optical purity of the amino acid product does not exceed 5%.

18. The process of claim 17, wherein the loss of optical purity of the amino acid product does not exceed 2%.

19. The process of claim 18, wherein the loss of optical purity of the amino acid product does not exceed 1%.

20. The process of claim 1, wherein the amino-protecting group of $P^1$ and/or $P^2$ is selected from the group consisting of t-butoxycarbonyl, acetyl, formyl, trifluoroacetyl and phthaloyl.

21. A process for producing an amino acid derivative represented by formula (I):

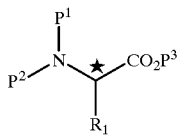
(I)

wherein:
R$^1$ represents an unsubstituted or substituted cyclohexyl group having 6 to 15 carbon atoms or an unsubstituted or substituted cyclohexylalkyl group having 7 to 15 carbon atoms;
P$^1$ and P$^2$ each, independently, represent a hydrogen atom or an amino-protecting group, or P$^1$ and P$^2$ together form a difunctional amino-protecting group;
P$^3$ represents a hydrogen atom or a carboxyl-protecting group; and
★ represents an asymmetric carbon atom, comprising:
hydrogenating an aromatic amino acid derivative of formula (II) below having an optical purity of at least 5% ee in the presence of a ruthenium catalyst in a solvent containing a base, such that the loss of optical purity of the amino acid product (I) does not exceed 10%:

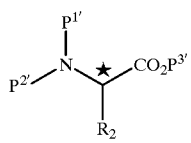
(II)

wherein:
R$^2$ represents an unsubstituted or substituted aryl group having 6 to 15 carbon atoms or an unsubstituted or substituted aralkyl group having 7 to 15 carbon atoms;
P$^{1'}$ and P$^{2'}$ each, independently, represent a hydrogen atom or an amino-protecting group, or a P$^{1'}$ and P$^{2'}$, together, form a difunctional amino-protecting group;
P$^{3'}$ represents a hydrogen atom or a carboxyl-protecting group; and
★ is as defined above.

22. The process of claim 21, wherein the optical purity of the reactant amino acid derivative (II) is at least 10% ee.

23. The process of claim 21, wherein the loss of optical purity of the amino acid product (I) does not exceed 5%.

24. The process of claim 1, wherein said solvent contains 1 to 10 equivalents of base and the reaction is conducted at a reaction temperature ranging from room temperature to 250° C.

25. The process of claim 24, wherein the reaction temperature ranges from room temperature to 150° C.

26. The process of claim 25, wherein the reaction temperature ranges from 40 to 150° C.

27. The process of claim 16, herein said solvent contains 1 to 10 equivalents of base and the reaction is conducted at a reaction temperature ranging from room temperature to 250° C.

28. The process of claim 27, wherein the reaction temperature ranges from room temperature to 150° C.

29. The process of claim 28, wherein the reaction temperature ranges from 40 to 150° C.

30. The process of claim 21, wherein said solvent contains 1 to 10 equivalents of base and the reaction is conducted at a reaction temperature ranging from room temperature to 250° C.

31. The process of claim 30, wherein the reaction temperature ranges from room temperature to 150° C.

32. The process of claim 31, wherein the reaction temperature ranges from 40 to 150° C.

33. A process for producing an amino acid derivative represented by formula (I):

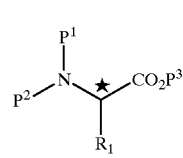
(I)

wherein:

R$^1$ represents an unsubstituted or substituted cyclohexyl group having 6 to 15 carbon atoms or an unsubstituted or substituted cyclohexylalkyl group having 7 to 15 carbon atoms;

P$^1$ and P$^2$ each, independently, represent a hydrogen atom or an amino-protecting group, or P$^1$ and P$^2$ together form a difunctional amino-protecting group;

P$^3$ represents a hydrogen atom or carboxyl-protecting group; and

★ represents an asymmetric carbon atom, comprising:

hydrogenating an aromatic amino acid derivative represented by formula (II) under basic conditions in the presence of a ruthenium catalyst in a solvent containing from 1 to 10 equivalents of a base:

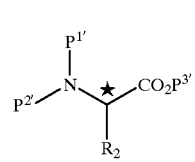
(II)

wherein:
R$^2$ represents an unsubstituted or substituted aryl group having 6 to 15 carbon atoms or an unsubstituted or substituted aralkyl group having 7 to 15 carbon atoms;
P$^{1'}$ and P$^{2'}$ each, independently, represent a hydrogen atom or an amino-protecting group, or a P$^{1'}$ and P$^{2'}$, together, form a difunctional amino-protecting group;
P$^{3'}$ represents a hydrogen atom or a carboxyl-protecting group; and
★ is as defined above.

34. A process for producing an amino acid derivative represented by formula (I):

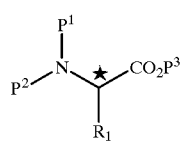

(I)

wherein:
- $R^1$ represents an unsubstituted or substituted cyclohexyl group having 6 to 15 carbon atoms or an unsubstituted or substituted cyclohexylalkyl group having 7 to 15 carbon atoms;
- $P^1$ and $P^2$ each, independently, represent a hydrogen atom or an amino-protecting group, or $P^1$ and $P^2$ together form a difunctional amino-protecting group;
- $P^3$ represents a hydrogen atom or carboxyl-protecting group; and
- ★ represents an asymmetric carbon atom, comprising:

hydrogenating an aromatic amino acid derivative of formula (II) below ranging in enantiomer constituency from a racemic mixture to 100% single enantiomer under basic conditions in the presence of a ruthenium catalyst in a solvent containing from 1 to 10 equivalents of a base such that as a result of reduction, the loss of optical purity of the amino acid product (I) does not exceed 10%:

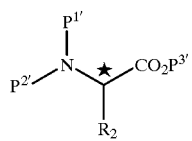

(II)

wherein:
- $R^2$ represents an unsubstituted or substituted aryl group having 6 to 15 carbon atoms or an unsubstituted or substituted aralkyl group having 7 to 15 carbon atoms;
- $P^{1'}$ and $P^{2'}$ each, independently, represent a hydrogen atom or an amino-protecting group, or a $P^{1'}$ and $P^{2'}$, together, form a difunctional amino-protecting group;
- $P^{3'}$ represents a hydrogen atom or a carboxyl-protecting group; and
- ★ is as defined above.

35. A process for producing an amino acid derivative represented by formula (I):

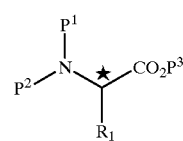

(I)

wherein:
- $R^1$ represents an unsubstituted or substituted cyclohexyl group having 6 to 15 carbon atoms or an unsubstituted or substituted cyclohexylalkyl group having 7 to 15 carbon atoms;
- $P^1$ and $P^2$ each, independently, represent a hydrogen atom or an amino-protecting group, or $P^1$ and $P^2$ together form a difunctional amino-protecting group;
- $P^3$ represents a hydrogen atom or a carboxyl-protecting group; and
- ★ represents an asymmetric carbon atom, comprising:

hydrogenating an aromatic amino acid derivative of formula (II) below having an optical purity of at least 5% ee under basic conditions in the presence of a ruthenium catalyst in a solvent containing from 1 to 10 equivalents of a base, such that the loss of optical purity of the amino acid product (I) does not exceed 10%:

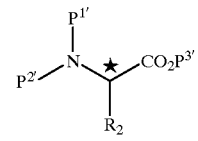

(II)

wherein:
- $R^2$ represents an unsubstituted or substituted aryl group having 6 to 15 carbon atoms or an unsubstituted or substituted aralkyl group having 7 to 15 carbon atoms;
- $P^{1'}$ and $P^{2'}$ each, independently, represent a hydrogen atom or an amino-protecting group, or a $P^{1'}$ and $P^{2'}$, together, form a difunctional amino-protecting group;
- $P^{3'}$ represents a hydrogen atom or a carboxyl-protecting group; and
- ★ is as defined above.

* * * * *